(12) United States Patent
Cao et al.

(10) Patent No.: US 11,517,275 B2
(45) Date of Patent: Dec. 6, 2022

(54) APPARATUS FOR IMAGING THE PROSTATE

(71) Applicant: SHENZHEN XPECTVISION TECHNOLOGY CO., LTD., Shenzhen (CN)

(72) Inventors: Peiyan Cao, Shenzhen (CN); Yurun Liu, Shenzhen (CN)

(73) Assignee: SHENZHEN XPECTVISION TECHNOLOGY CO., LTD., Shenzhen (CN)

( * ) Notice: Subject to any disclaimer, the term of this patent is extended or adjusted under 35 U.S.C. 154(b) by 37 days.

(21) Appl. No.: 17/081,520

(22) Filed: Oct. 27, 2020

(65) Prior Publication Data

US 2021/0038177 A1 Feb. 11, 2021

Related U.S. Application Data

(63) Continuation of application No. PCT/CN2018/086651, filed on May 14, 2018.

(51) Int. Cl.
*A61B 6/00* (2006.01)
*G01T 1/161* (2006.01)

(52) U.S. Cl.
CPC ............ *A61B 6/425* (2013.01); *A61B 6/4233* (2013.01); *A61B 6/4241* (2013.01); *A61B 6/50* (2013.01); *A61B 6/54* (2013.01); *G01T 1/161* (2013.01)

(58) Field of Classification Search
CPC ..... A61B 6/425; A61B 6/4233; A61B 6/4241; A61B 6/50; A61B 6/54; G01T 1/161
See application file for complete search history.

(56) References Cited

U.S. PATENT DOCUMENTS

| | | | | |
|---|---|---|---|---|
| 4,437,161 A | * | 3/1984 | Anderson | H04N 5/3205 378/98.12 |
| 2003/0141906 A1 | * | 7/2003 | Tumer | H04N 5/335 348/E5.091 |
| 2003/0223534 A1 | | 12/2003 | Sato et al. | |
| 2004/0092807 A1 | | 5/2004 | Breskin et al. | |
| 2004/0239377 A1 | * | 12/2004 | Tumer | G01T 1/17 327/94 |
| 2007/0114427 A1 | * | 5/2007 | Aoki | G01T 1/247 250/370.09 |
| 2007/0161885 A1 | * | 7/2007 | Kimchy | A61B 5/42 600/407 |
| 2009/0039273 A1 | * | 2/2009 | Tkaczyk | G01T 1/247 250/370.06 |
| 2010/0020924 A1 | * | 1/2010 | Steadman Booker | G01T 1/17 378/19 |
| 2011/0286576 A1 | | 11/2011 | Cui et al. | |

(Continued)

FOREIGN PATENT DOCUMENTS

| | | |
|---|---|---|
| CN | 1897873 A | 1/2007 |
| CN | 102596044 A | 7/2012 |

(Continued)

*Primary Examiner* — Blake C Riddick
(74) *Attorney, Agent, or Firm* — IPro, PLLC; Qian Gu

(57) ABSTRACT

Disclosed herein is an apparatus comprising an insertion tube; an image sensor inside the insertion tube; wherein the image sensor comprises an array of pixels; wherein the image sensor is configured to count numbers of particles of radiation incident on the pixels, within a period of time. Also disclosed herein is a method of using this apparatus.

24 Claims, 12 Drawing Sheets

(56) References Cited

U.S. PATENT DOCUMENTS

| | | | |
|---|---|---|---|
| 2012/0230574 A1* | 9/2012 | Rozenfeld | A61B 8/12 600/436 |
| 2013/0010921 A1* | 1/2013 | Sagoh | A61B 6/4233 250/366 |
| 2013/0105701 A1* | 5/2013 | Han | G01T 1/366 250/336.1 |
| 2014/0016239 A1* | 1/2014 | Kim | H02H 3/006 327/279 |
| 2014/0249402 A1 | 9/2014 | Kimchy et al. | |
| 2014/0257088 A1 | 9/2014 | D'Andrea | |
| 2014/0270064 A1* | 9/2014 | Oh | A61B 6/484 378/53 |
| 2014/0334600 A1* | 11/2014 | Lee | A61B 6/482 250/336.1 |
| 2014/0369472 A1* | 12/2014 | Oh | A61B 6/4417 378/62 |
| 2015/0063527 A1* | 3/2015 | Daerr | G01T 1/171 378/5 |
| 2016/0278723 A1 | 9/2016 | Majewski et al. | |
| 2017/0205284 A1* | 7/2017 | De Geronimo | G01J 1/44 |
| 2019/0277798 A1* | 9/2019 | Ferrão De Paiva Martins | G01N 27/414 |

FOREIGN PATENT DOCUMENTS

| | | |
|---|---|---|
| CN | 107507844 A | 12/2017 |
| CN | 107533146 A | 1/2018 |
| CN | 107615095 A | 1/2018 |
| CN | 111587084 A | 8/2020 |
| TW | 201730583 A | 9/2017 |
| WO | 2016161544 A1 | 10/2016 |
| WO | 2019148477 A1 | 8/2019 |

* cited by examiner

APPARATUS FOR IMAGING THE PROSTATE

BACKGROUND

Image sensors based on radiation detectors may be devices used to measure the flux, spatial distribution, spectrum or other properties of radiation such as X-rays. These image sensors may be used for many applications. One important application is medical imaging in which the internal structure of a non-uniformly composed and opaque object such as the human body may be revealed.

The prostate is a gland of the male reproductive system in human. The prostate secretes a slightly alkaline fluid that constitutes about 30% of the volume of semen. The alkalinity of semen helps prolonging the lifespan of sperms. Prostate diseases are common, and the risk increases with age. Medical imaging (e.g., radiography) can help diagnosis of prostate diseases. However, because the prostate is deep inside the human body, imaging the prostate may be difficult. For example, the thick tissues around the prostate may reduce the imaging resolution or increase the dose of radiation sufficient for imaging.

SUMMARY

Disclosed herein is an endoscope comprising: an insertion tube; a radiation detector configured to detect radiation particles in a first range of energy and radiation particles in a second range of energy.

According to an embodiment,

Disclosed herein is an apparatus comprising: an insertion tube; an image sensor inside the insertion tube; wherein the image sensor comprises an array of pixels; wherein the image sensor is configured to count numbers of particles of radiation incident on the pixels, within a period of time.

According to an embodiment, the insertion tube is configured to be inserted into the rectum of a human.

According to an embodiment, the image sensor comprises a plurality of chips mounted on a substrate, wherein the pixels are distributed among the plurality of chips.

According to an embodiment, the image sensor is flexible.

According to an embodiment, the particles of radiation are X-ray photons.

According to an embodiment, the X-ray photons have energies between 20 keV and 30 keV.

According to an embodiment, the image sensor comprises: a radiation absorption layer comprising an electric contact; a first voltage comparator configured to compare a voltage of the electric contact to a first threshold; a second voltage comparator configured to compare the voltage to a second threshold; a counter configured to register at least one of the numbers; a controller; wherein the controller is configured to start a time delay from a time at which the first voltage comparator determines that an absolute value of the voltage equals or exceeds an absolute value of the first threshold; wherein the controller is configured to activate the second voltage comparator during the time delay; wherein the controller is configured to cause the at least one of the numbers to increase by one, when the second voltage comparator determines that an absolute value of the voltage equals or exceeds an absolute value of the second threshold.

According to an embodiment, the apparatus further comprises an integrator electrically connected to the electric contact, wherein the integrator is configured to collect charge carriers from the electric contact.

According to an embodiment, the controller is configured to activate the second voltage comparator at a beginning or expiration of the time delay.

According to an embodiment, the controller is configured to connect the electric contact to an electrical ground.

According to an embodiment, a rate of change of the voltage is substantially zero at expiration of the time delay.

According to an embodiment, the radiation absorption layer comprises a diode.

According to an embodiment, the radiation absorption layer comprises single-crystalline silicon.

According to an embodiment, the image sensor does not comprise a scintillator.

Disclosed herein is a system comprising the apparatus above, and a radiation source.

Disclosed is a method comprising: inserting, into the rectum of a human, an insertion tube with an image sensor therein, the image sensor comprising an array of pixels; directing radiation toward the prostate of the human; counting numbers of particles of radiation incident on the pixels, within a period of time; obtaining an image of the prostate based on the numbers.

According to an embodiment, the image sensor comprises a plurality of chips mounted on a substrate, wherein the pixels are distributed among the plurality of chips.

According to an embodiment, the image sensor is flexible.

According to an embodiment, the particles of radiation are X-ray photons.

According to an embodiment, the X-ray photons have energies between 20 keV and 30 keV.

According to an embodiment, the image sensor comprises: a radiation absorption layer comprising an electric contact; a first voltage comparator configured to compare a voltage of the electric contact to a first threshold; a second voltage comparator configured to compare the voltage to a second threshold; a counter configured to register at least one of the numbers; a controller; wherein the controller is configured to start a time delay from a time at which the first voltage comparator determines that an absolute value of the voltage equals or exceeds an absolute value of the first threshold; wherein the controller is configured to activate the second voltage comparator during the time delay; wherein the controller is configured to cause the at least one of the numbers to increase by one, when the second voltage comparator determines that an absolute value of the voltage equals or exceeds an absolute value of the second threshold.

According to an embodiment, the image sensor further comprises an integrator electrically connected to the electric contact, wherein the integrator is configured to collect charge carriers from the electric contact.

According to an embodiment, the controller is configured to activate the second voltage comparator at a beginning or expiration of the time delay.

According to an embodiment, the controller is configured to connect the electric contact to an electrical ground.

According to an embodiment, a rate of change of the voltage is substantially zero at expiration of the time delay.

According to an embodiment, the radiation absorption layer comprises a diode.

According to an embodiment, the radiation absorption layer comprises single-crystalline silicon.

According to an embodiment, the image sensor does not comprise a scintillator.

DETAILED DESCRIPTION

Figure 1:
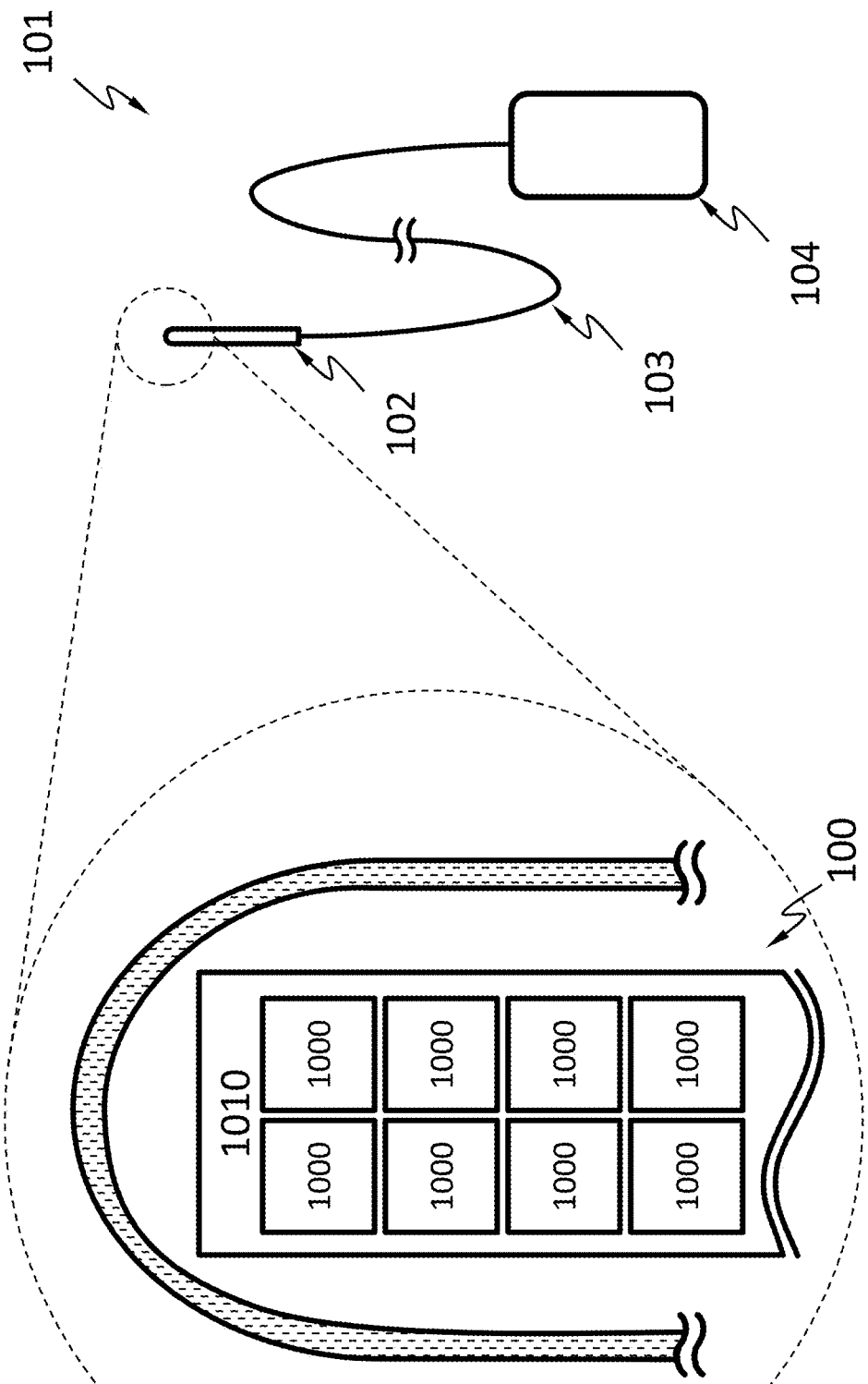
FIG. 1 schematically shows an apparatus, according to an embodiment.

FIG. 1 schematically shows an apparatus 101, according to an embodiment. The apparatus 101 has an insertion tube 102, which may be rigid or flexible. The apparatus 101 may have a signal cable 103 and a control unit 104. The control unit 104 may be configured to receive or transmit signals or control the movement of the insertion tube 102, through the signal cable 103. The insertion tube 102 may have a small diameter (e.g., less than 50 mm), which is suitable for inserting into the rectum of a human. The insertion tube 102 may be transparent to a radiation of interest and may encapsulate an image sensor 100. The image sensor 100 may be hermetically sealed inside by the insertion tube 102 to protect the image sensor 100 from bodily fluids.

Figure 2A:
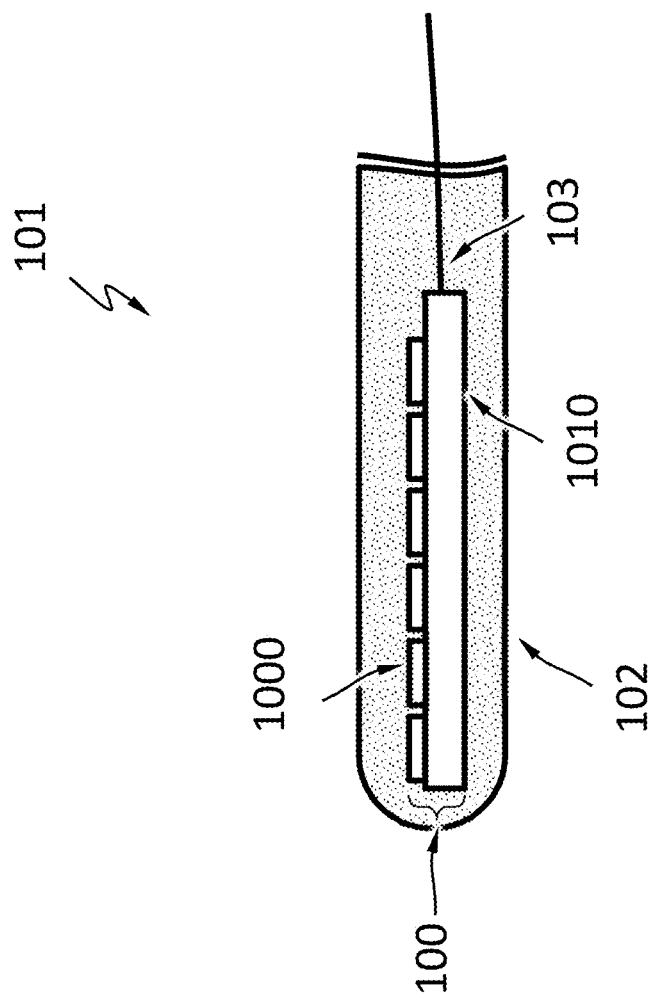
FIG. 2A and FIG. 2B schematically show a portion of the apparatus, according to an embodiment.
Figure 2B:
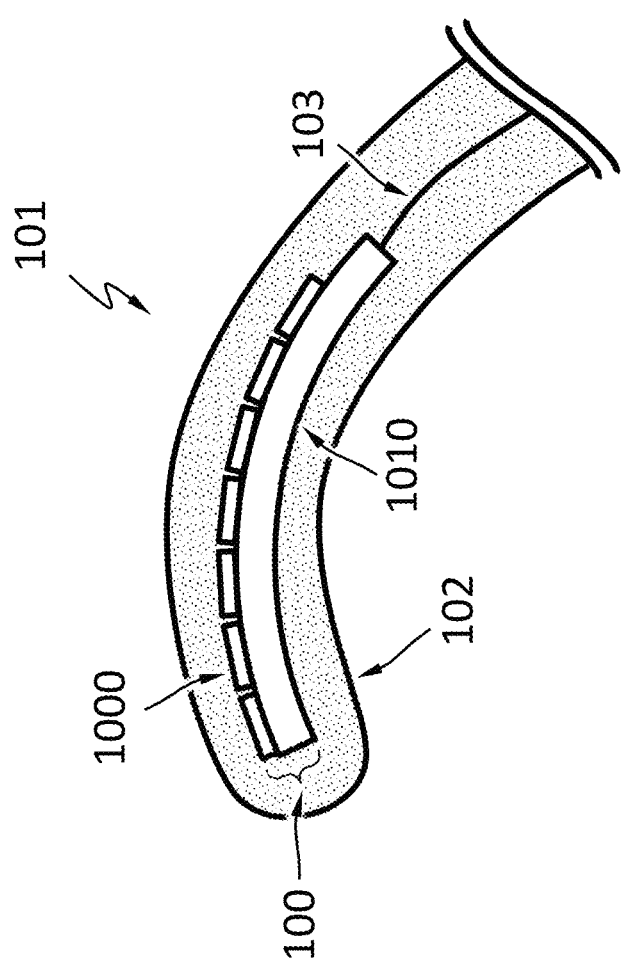

FIG. 2A and FIG. 2B schematically show a portion of the apparatus 101, according to an embodiment. The image sensor 100 may include multiple chips 1000 mounted on a substrate 1010. The substrate 1010 may be a printed circuit board. The substrate 1010 may be electrically connected to the chips 1000 and to the signal cable 103. In the example of FIG. 2A, the image sensor 100 is rigid and so is the substrate 1010. In the example of FIG. 2B, the image sensor 100 is flexible and so is the substrate 1010.

Figure 3:
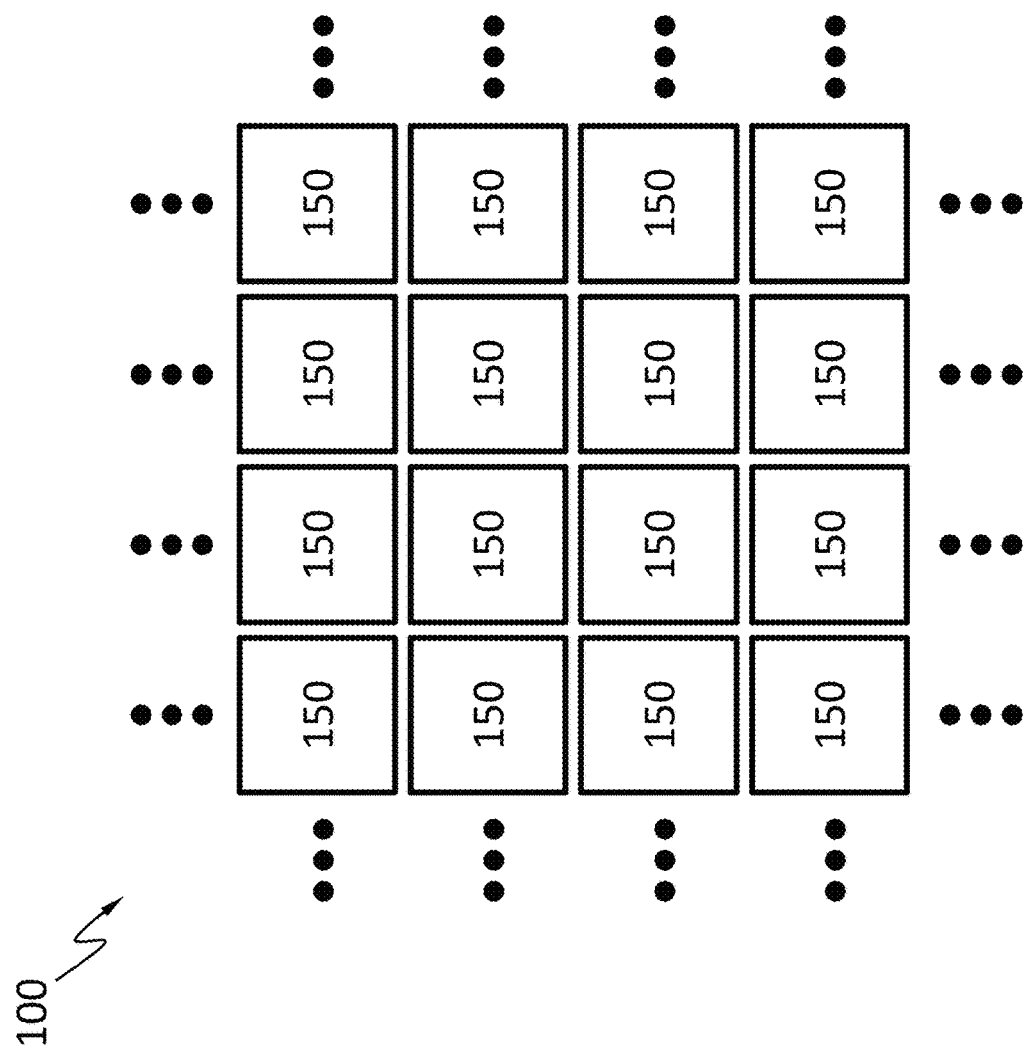
FIG. 3 schematically shows that an image sensor having an array of pixels, according to an embodiment.

FIG. 3 schematically shows that the image sensor 100 may have an array of pixels 150, according to an embodiment. When the image sensor 100 has multiple chips 1000, the pixels 150 may be distributed among the multiple chips 1000. For example, the chips 1000 may each contain some of the pixels 150 of the image sensor 100. The array of the pixels 150 may be a rectangular array, a honeycomb array, a hexagonal array or any other suitable array. The image sensor 100 may count the numbers of particles of radiation incident on the pixels 150, within a period of time. An example of the particles of radiation is X-ray photons. The X-ray photons may have suitable energies such as energies between 20 keV and 30 keV. Each pixel 150 may be configured to measure its dark current, such as before or concurrently with each particle of radiation incident thereon. The pixels 150 may be configured to operate in parallel. For example, the image sensor 100 may count one particle of radiation incident on one pixel 150 before, after or while the image sensor 100 counts another particle of radiation incident on another pixel 150. The pixels 150 may be individually addressable.

Figure 4A:
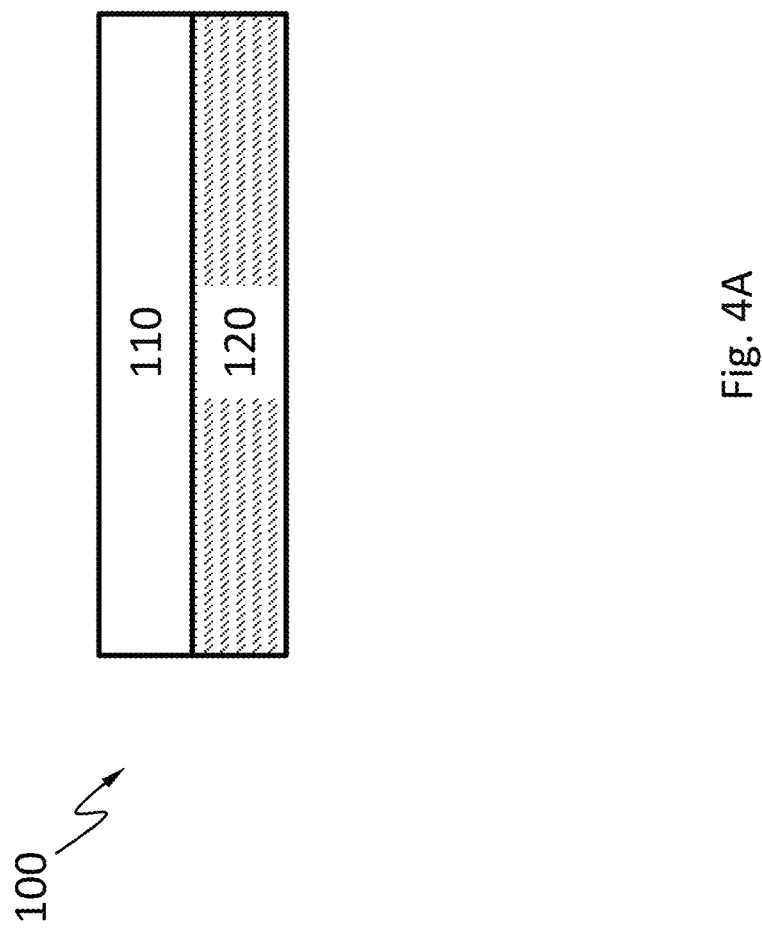
FIG. 4A shows a cross-sectional schematic of the image sensor, according to an embodiment.

FIG. 4A shows a cross-sectional schematic of the image sensor 100, according to an embodiment. The image sensor 100 may include a radiation absorption layer 110 and an electronics layer 120 (e.g., an ASIC) for processing or analyzing electrical signals incident particles of radiation generate in the radiation absorption layer 110. The image sensor 100 may or may not include a scintillator. The radiation absorption layer 110 may include a semiconductor material such as single-crystalline silicon. The semiconductor may have a high mass attenuation coefficient for the radiation of interest.

Figure 4B:
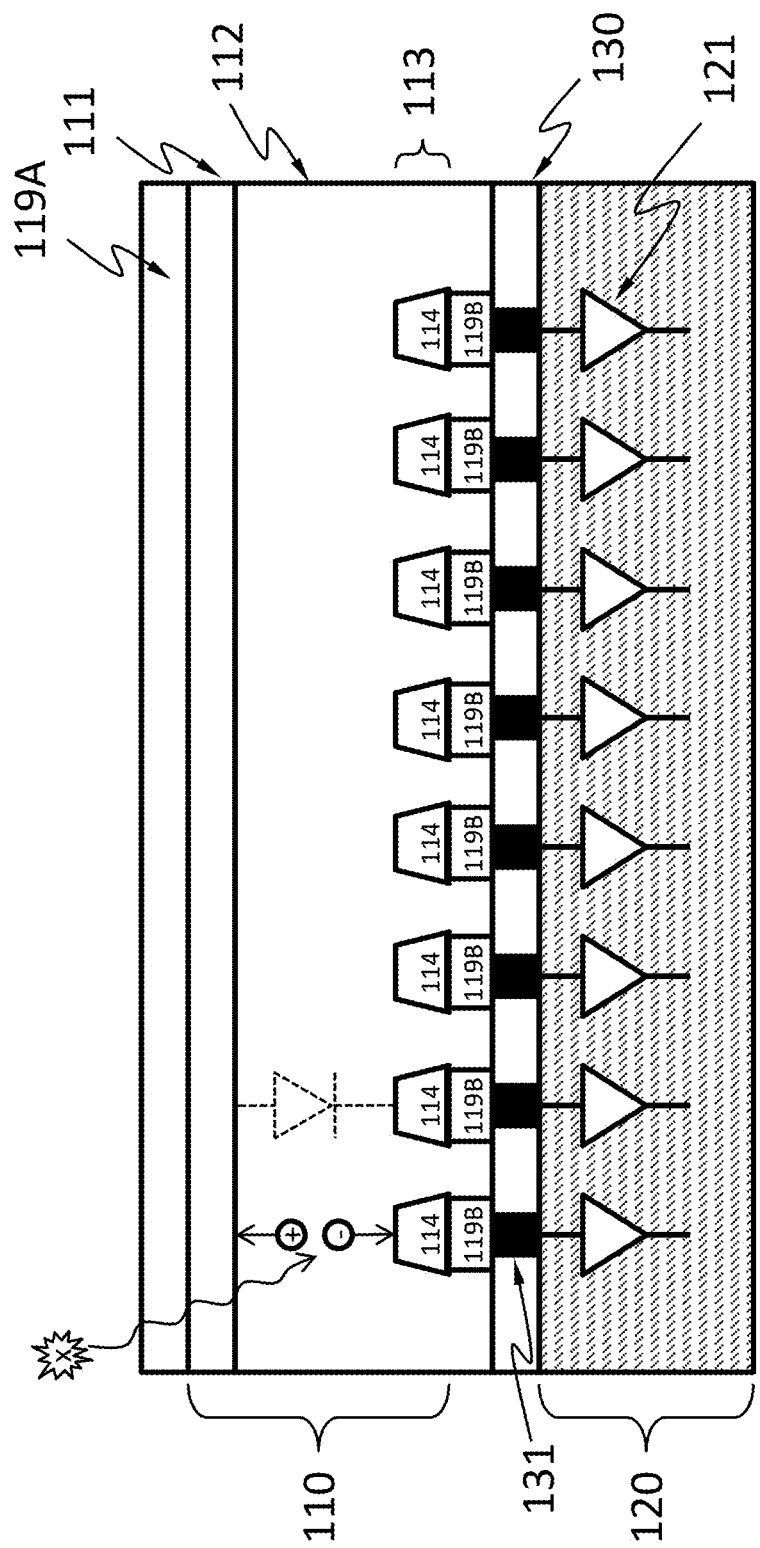
FIG. 4B shows a detailed cross-sectional schematic of the image sensor, according to an embodiment.

As shown in a more detailed cross-sectional schematic of the image sensor 100 in FIG. 4B, according to an embodiment, the radiation absorption layer 110 may include one or more diodes (e.g., p-i-n or p-n) formed by a first doped region 111, one or more discrete regions 114 of a second doped region 113. The second doped region 113 may be separated from the first doped region 111 by an optional the intrinsic region 112. The discrete regions 114 are separated from one another by the first doped region 111 or the intrinsic region 112. The first doped region 111 and the second doped region 113 have opposite types of doping (e.g., region 111 is p-type and region 113 is n-type, or region 111 is n-type and region 113 is p-type). In the example in FIG. 4B, each of the discrete regions 114 of the second doped region 113 forms a diode with the first doped region 111 and the optional intrinsic region 112. Namely, in the example in FIG. 4B, the radiation absorption layer 110 has a plurality of diodes having the first doped region 111 as a shared electrode. The first doped region 111 may also have discrete portions. The radiation absorption layer 110 may have an electric contact 119A in electrical contact with the first doped region 111. The radiation absorption layer 110 may have multiple discrete electric contacts 119B, each of which is in electrical contact with the discrete regions 114.

When particles of radiation hit the radiation absorption layer 110 including diodes, the particles of radiation may be absorbed and generate one or more charge carriers by a number of mechanisms. The charge carriers may drift to the electric contacts 119A and 119B under an electric field. The field may be an external electric field. In an embodiment, the charge carriers may drift in directions such that the charge carriers generated by a single particle of the radiation are not substantially shared by two different discrete regions 114 ("not substantially shared" here means less than 2%, less than 0.5%, less than 0.1%, or less than 0.01% of these charge carriers flow to a different one of the discrete regions 114 than the rest of the charge carriers). Charge carriers generated by a particle of the radiation incident around the footprint of one of these discrete regions 114 are not substantially shared with another of these discrete regions 114. A pixel 150 associated with a discrete region 114 may be an area around the discrete region 114 in which substantially all (more than 98%, more than 99.5%, more than 99.9%, or more than 99.99% of) charge carriers generated by a particle of the radiation incident therein flow to the discrete region 114. Namely, less than 2%, less than 1%, less than 0.1%, or less than 0.01% of these charge carriers flow beyond the pixel 150.

Figure 4C:
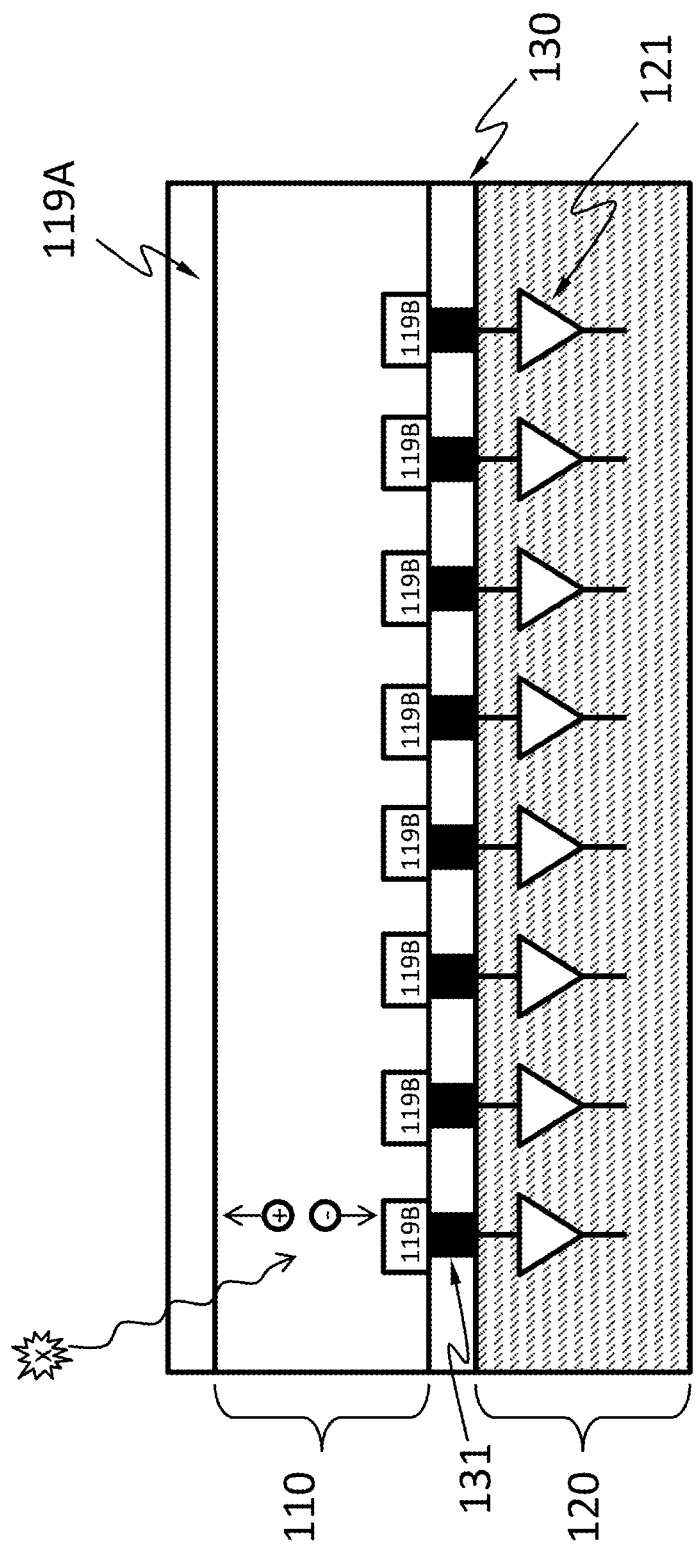
FIG. 4C shows an alternative detailed cross-sectional schematic of the image sensor, according to an embodiment.

As shown in an alternative detailed cross-sectional schematic of the image sensor 100 in FIG. 4C, according to an embodiment, the radiation absorption layer 110 may include a resistor of a semiconductor material such as single-crystalline silicon but does not include a diode. The semiconductor may have a high mass attenuation coefficient for the radiation of interest. The radiation absorption layer 110 may have an electric contact 119A in electrical contact with the semiconductor on one surface of the semiconductor. The radiation absorption layer 110 may have multiple electric contacts 119B on another surface of the semiconductor.

When particles of radiation hit the radiation absorption layer 110 including a resistor but not diodes, the particles of radiation may be absorbed and generate one or more charge carriers by a number of mechanisms. A particle of the radiation may generate 10 to 100000 charge carriers. The charge carriers may drift to the electrical contacts 119A and 119B under an electric field. The field may be an external electric field. In an embodiment, the charge carriers may drift in directions such that the charge carriers generated by a single particle of the radiation are not substantially shared by two electrical contacts 119B ("not substantially shared" here means less than 2%, less than 0.5%, less than 0.1%, or less than 0.01% of these charge carriers flow to a different one of the discrete portions than the rest of the charge carriers). Charge carriers generated by a particle of the radiation incident around the footprint of one of the electrical contacts 119B are not substantially shared with another of the electrical contacts 119B. A pixel 150 associated with one of the electrical contacts 119B may be an area around it in which substantially all (more than 98%, more than 99.5%, more than 99.9% or more than 99.99% of) charge carriers generated by a particle of the radiation incident therein flow to that one electrical contact 119B. Namely, less than 2%, less than 0.5%, less than 0.1%, or less than 0.01% of these charge carriers flow beyond the pixel associated with that one electrical contact 119B.

The electronics layer 120 may include an electronic system 121 suitable for processing or interpreting signals generated by the radiation incident on the radiation absorption layer 110. The electronic system 121 may include an analog circuitry such as a filter network, amplifiers, integrators, and comparators, or a digital circuitry such as a microprocessors, and memory. The electronic system 121 may include one or more ADCs. The electronic system 121 may include components shared by the pixels or components dedicated to a single pixel. For example, the electronic system 121 may include an amplifier dedicated to each pixel 150 and a microprocessor shared among all the pixels 150. The electronic system 121 may be electrically connected to the pixels by vias 131. Space among the vias may be filled with a filler material 130, which may increase the mechanical stability of the connection of the electronics layer 120 to the radiation absorption layer 110. Other bonding techniques are possible to connect the electronic system 121 to the pixels without using vias.

Figure 5A:
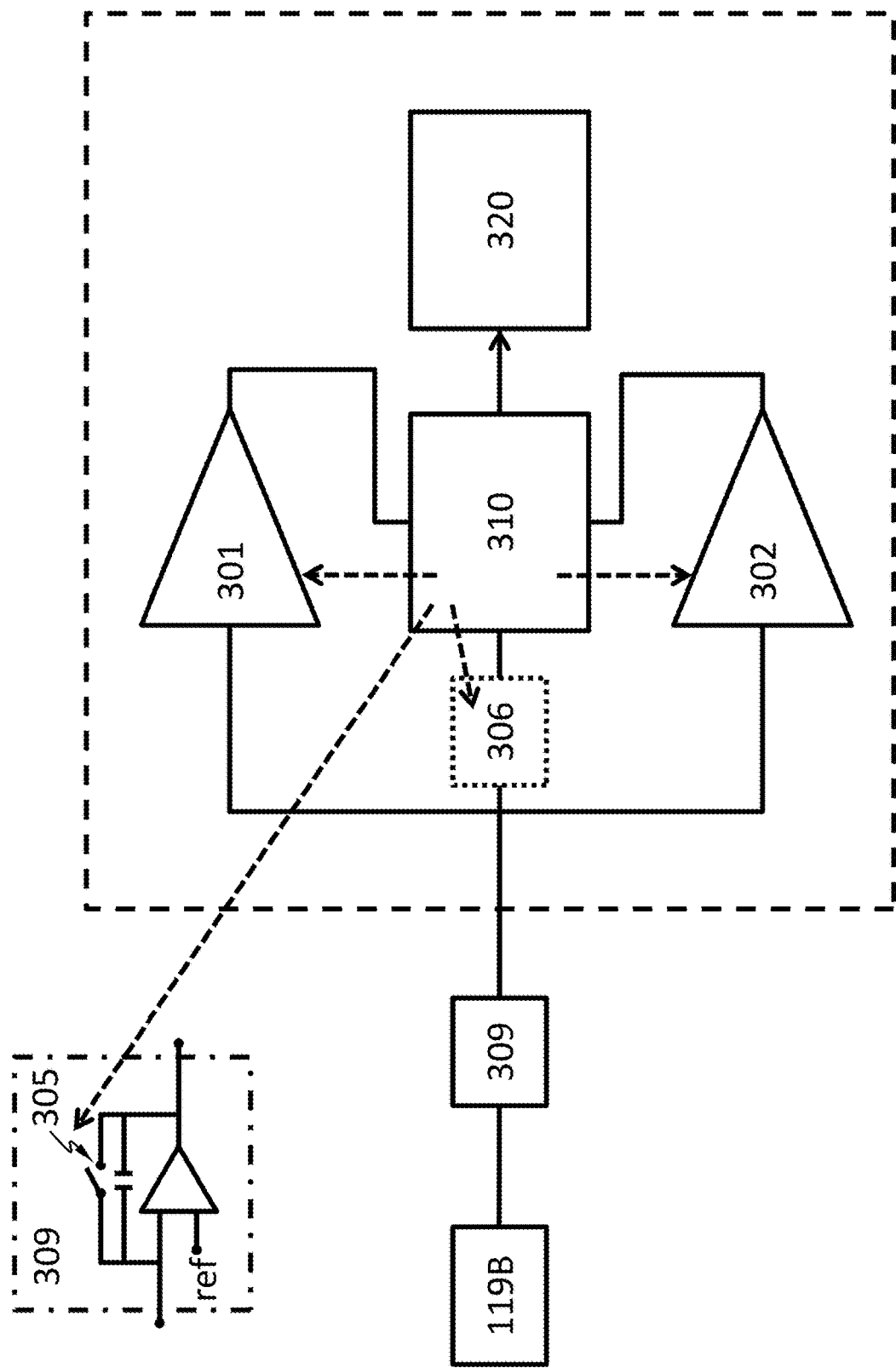
FIG. 5A and FIG. 5B each show a component diagram of an electronic system of the image sensor, according to an embodiment.
Figure 5B:
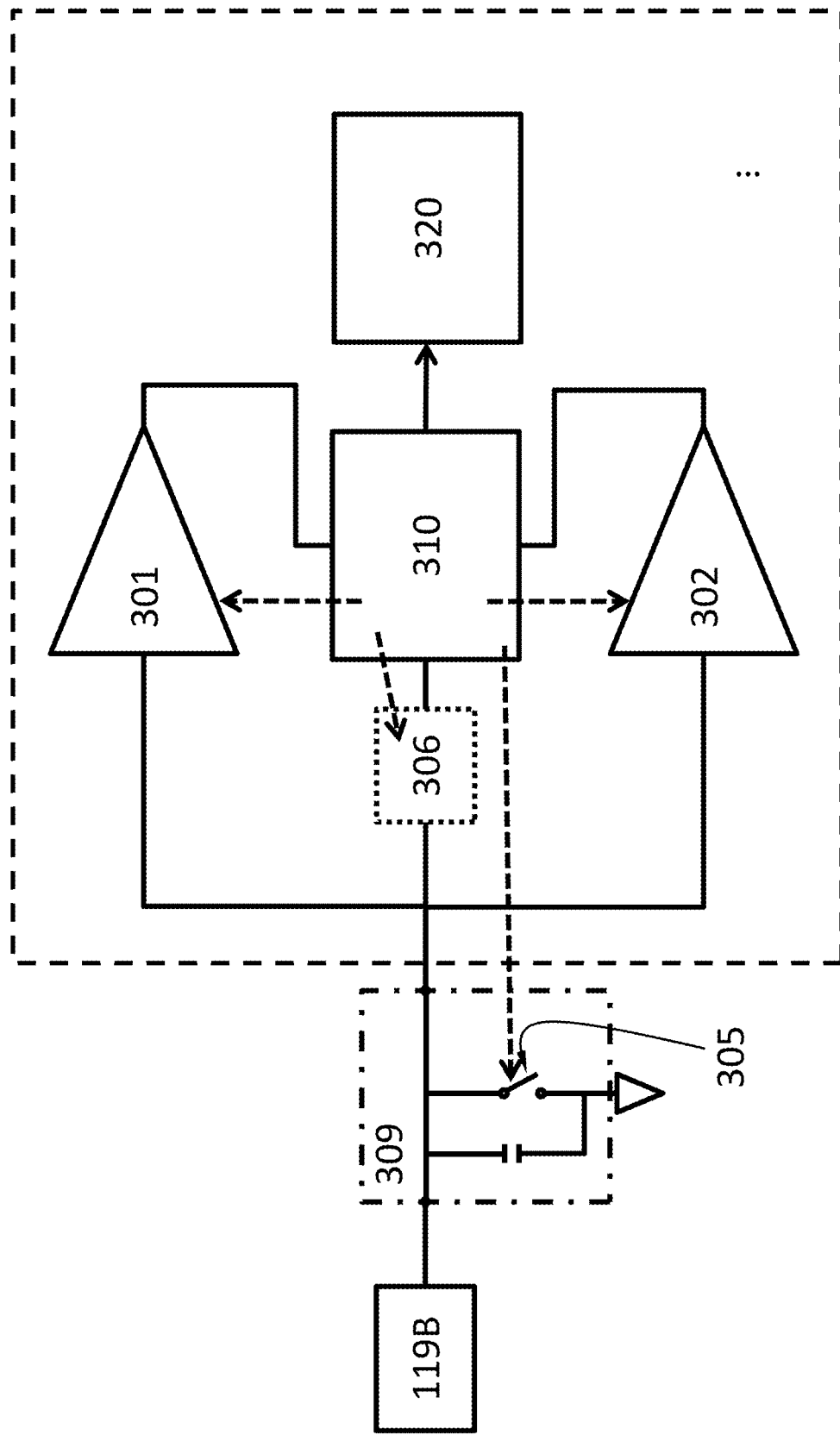

FIG. 5A and FIG. 5B each show a component diagram of the electronic system 121, according to an embodiment. The electronic system 121 may include a first voltage comparator 301, a second voltage comparator 302, a counter 320, a switch 305, an optional voltmeter 306 and a controller 310.

The first voltage comparator 301 is configured to compare the voltage of at least one of the electric contacts 119B to a first threshold. The first voltage comparator 301 may be configured to monitor the voltage directly, or calculate the voltage by integrating an electric current flowing through the electrical contact 119B over a period of time. The first voltage comparator 301 may be controllably activated or deactivated by the controller 310. The first voltage comparator 301 may be a continuous comparator. Namely, the first voltage comparator 301 may be configured to be activated continuously and monitor the voltage continuously. The first voltage comparator 301 may be a clocked comparator. The first threshold may be 5-10%, 10%-20%, 20-30%, 30-40% or 40-50% of the maximum voltage one incident particle of radiation may generate on the electric contact 119B. The maximum voltage may depend on the energy of the incident particle of radiation, the material of the radiation absorption layer 110, and other factors. For example, the first threshold may be 50 mV, 100 mV, 150 mV, or 200 mV.

The second voltage comparator 302 is configured to compare the voltage to a second threshold. The second voltage comparator 302 may be configured to monitor the voltage directly or calculate the voltage by integrating an electric current flowing through the diode or the electrical contact over a period of time. The second voltage comparator 302 may be a continuous comparator. The second voltage comparator 302 may be controllably activate or deactivated by the controller 310. When the second voltage comparator 302 is deactivated, the power consumption of the second voltage comparator 302 may be less than 1%, less than 5%, less than 10% or less than 20% of the power consumption when the second voltage comparator 302 is activated. The absolute value of the second threshold is greater than the absolute value of the first threshold. As used herein, the term "absolute value" or "modulus" |x| of a real number x is the non-negative value of x without regard to its sign. Namely, $$|x| = \begin{cases} x, & \text{if } x \geq 0 \\ -x, & \text{if } x \leq 0 \end{cases}.$$

The second threshold may be 200%-300% of the first threshold. The second threshold may be at least 50% of the maximum voltage one incident particle of radiation may generate on the electric contact 119B. For example, the second threshold may be 100 mV, 150 mV, 200 mV, 250 mV or 300 mV. The second voltage comparator 302 and the first voltage comparator 310 may be the same component. Namely, the system 121 may have one voltage comparator that can compare a voltage with two different thresholds at different times.

The first voltage comparator 301 or the second voltage comparator 302 may include one or more op-amps or any other suitable circuitry. The first voltage comparator 301 or the second voltage comparator 302 may have a high speed to allow the system 121 to operate under a high flux of incident particles of radiation. However, having a high speed is often at the cost of power consumption.

The counter 320 is configured to register at least a number of particles of radiation incident on the pixel 150 encompassing the electric contact 119B. The counter 320 may be a software component (e.g., a number stored in a computer memory) or a hardware component (e.g., a 4017 IC and a 7490 IC).

The controller 310 may be a hardware component such as a microcontroller and a microprocessor. The controller 310 is configured to start a time delay from a time at which the first voltage comparator 301 determines that the absolute value of the voltage equals or exceeds the absolute value of the first threshold (e.g., the absolute value of the voltage increases from below the absolute value of the first threshold to a value equal to or above the absolute value of the first threshold). The absolute value is used here because the voltage may be negative or positive, depending on whether the voltage of the cathode or the anode of the diode or which electrical contact is used. The controller 310 may be configured to keep deactivated the second voltage comparator 302, the counter 320 and any other circuits the operation of the first voltage comparator 301 does not require, before the time at which the first voltage comparator 301 determines that the absolute value of the voltage equals or exceeds the absolute value of the first threshold. The time delay may expire before or after the voltage becomes stable, i.e., the rate of change of the voltage is substantially zero. The phase "the rate of change of the voltage is substantially zero" means that temporal change of the voltage is less than 0.1%/ns. The phase "the rate of change of the voltage is substantially non-zero" means that temporal change of the voltage is at least 0.1%/ns.

The controller 310 may be configured to activate the second voltage comparator during (including the beginning and the expiration) the time delay. In an embodiment, the controller 310 is configured to activate the second voltage comparator at the beginning of the time delay. The term "activate" means causing the component to enter an operational state (e.g., by sending a signal such as a voltage pulse or a logic level, by providing power, etc.). The term "deactivate" means causing the component to enter a non-operational state (e.g., by sending a signal such as a voltage pulse or a logic level, by cut off power, etc.). The operational state may have higher power consumption (e.g., 10 times higher, 100 times higher, 1000 times higher) than the non-operational state. The controller 310 itself may be deactivated until the output of the first voltage comparator 301 activates the controller 310 when the absolute value of the voltage equals or exceeds the absolute value of the first threshold.

The controller 310 may be configured to cause the number registered by the counter 320 to increase by one, if, during the time delay, the second voltage comparator 302 determines that the absolute value of the voltage equals or exceeds the absolute value of the second threshold.

The controller 310 may be configured to cause the optional voltmeter 306 to measure the voltage upon expiration of the time delay. The controller 310 may be configured to connect the electric contact 119B to an electrical ground, so as to reset the voltage and discharge any charge carriers accumulated on the electric contact 119B. In an embodiment, the electric contact 119B is connected to an electrical ground after the expiration of the time delay. In an embodiment, the electric contact 119B is connected to an electrical ground for a finite reset time period. The controller 310 may connect the electric contact 119B to the electrical ground by controlling the switch 305. The switch may be a transistor such as a field-effect transistor (FET).

In an embodiment, the system 121 has no analog filter network (e.g., a RC network). In an embodiment, the system 121 has no analog circuitry.

The voltmeter 306 may feed the voltage it measures to the controller 310 as an analog or digital signal.

The electronic system 121 may include an integrator 309 electrically connected to the electric contact 119B, wherein the integrator is configured to collect charge carriers from the electric contact 119B. The integrator 309 can include a capacitor in the feedback path of an amplifier. The amplifier configured as such is called a capacitive transimpedance amplifier (CTIA). CTIA has high dynamic range by keeping the amplifier from saturating and improves the signal-to-noise ratio by limiting the bandwidth in the signal path. Charge carriers from the electric contact 119B accumulate on the capacitor over a period of time ("integration period"). After the integration period has expired, the capacitor voltage is sampled and then reset by a reset switch. The integrator 309 can include a capacitor directly connected to the electric contact 119B.

Figure 6:
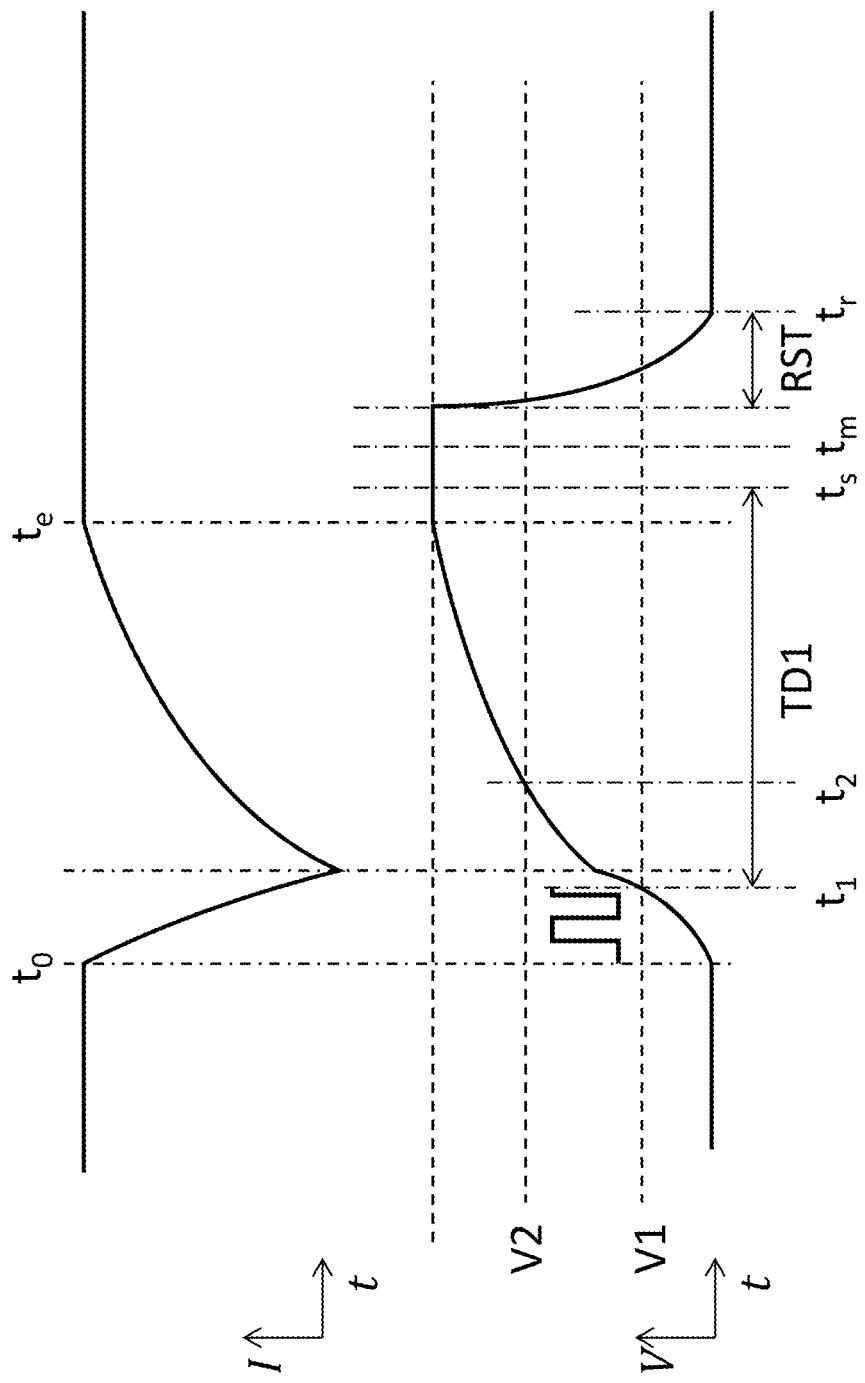
FIG. 6 schematically shows a temporal change of the electric current flowing through an electric contact (upper curve) of the radiation absorption layer of the image sensor, and a corresponding temporal change of the voltage on the electric contact (lower curve).

FIG. 6 schematically shows a temporal change of the electric current flowing through the electric contact 119B (upper curve) caused by charge carriers generated by a particle of radiation incident on the pixel 150 encompassing the electric contact 119B, and a corresponding temporal change of the voltage of the electric contact 119B (lower curve). The voltage may be an integral of the electric current with respect to time. At time to, the particle of radiation hits pixel 150, charge carriers start being generated in the pixel 150, electric current starts to flow through the electric contact 119B, and the absolute value of the voltage of the electric contact 119B starts to increase. At time $t_1$, the first voltage comparator 301 determines that the absolute value of the voltage equals or exceeds the absolute value of the first threshold V1, and the controller 310 starts the time delay TD1 and the controller 310 may deactivate the first voltage comparator 301 at the beginning of TD1. If the controller 310 is deactivated before $t_1$, the controller 310 is activated at $t_1$. During TD1, the controller 310 activates the second voltage comparator 302. The term "during" a time delay as used here means the beginning and the expiration (i.e., the end) and any time in between. For example, the controller 310 may activate the second voltage comparator 302 at the expiration of TD1. If during TD1, the second voltage comparator 302 determines that the absolute value of the voltage equals or exceeds the absolute value of the second threshold V2 at time $t_2$, the controller 310 waits for stabilization of the voltage to stabilize. The voltage stabilizes at time $t_e$, when all charge carriers generated by the particle of radiation drift out of the radiation absorption layer 110. At time $t_s$, the time delay TD1 expires. At or after time $t_e$, the controller 310 causes the voltmeter 306 to digitize the voltage and determines which bin the energy of the particle of radiation falls in. The controller 310 then causes the number registered by the counter 320 corresponding to the bin to increase by one. In the example of FIG. 6, time $t_s$ is after time $t_e$; namely TD1 expires after all charge carriers generated by the particle of radiation drift out of the radiation absorption layer 110. If time $t_e$ cannot be easily measured, TD1 can be empirically chosen to allow sufficient time to collect essentially all charge carriers generated by a particle of radiation but not too long to risk have another incident particle of radiation. Namely, TD1 can be empirically chosen so that time $t_s$ is empirically after time $t_e$. Time $t_s$ is not necessarily after time $t_e$ because the controller 310 may disregard TD1 once V2 is reached and wait for time $t_e$. The rate of change of the difference between the voltage and the contribution to the voltage by the dark current is thus substantially zero at $t_e$. The controller 310 may be configured to deactivate the second voltage comparator 302 at expiration of TD1 or at $t_2$, or any time in between.

The voltage at time $t_e$ is proportional to the amount of charge carriers generated by the particle of radiation, which relates to the energy of the particle of radiation. The controller 310 may be configured to determine the energy of the particle of radiation, using the voltmeter 306.

After TD1 expires or digitization by the voltmeter 306, whichever later, the controller 310 connects the electric contact 119B to an electric ground for a reset period RST to allow charge carriers accumulated on the electric contact 119B to flow to the ground and reset the voltage. After RST, the system 121 is ready to detect another incident particle of radiation. If the first voltage comparator 301 has been deactivated, the controller 310 can activate it at any time before RST expires. If the controller 310 has been deactivated, it may be activated before RST expires.

Figure 7:
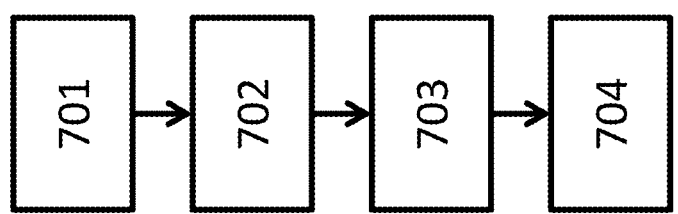
FIG. 7 shows an example flow chart for a method using the apparatus, according to an embodiment.

FIG. 7 shows an example flow chart for a method using the apparatus 101, according to an embodiment.

In procedure 701, the insertion tube 102 is inserted into the rectum of a human. In procedure 702, radiation (e.g., X-ray) is directed toward the prostate of the human. In procedure 703, the numbers of particles of radiation incident on the pixels 150 of the image sensor 100 within a period of time are counted. In procedure 704, an image of the prostate is obtained based on the numbers.

Figure 8:
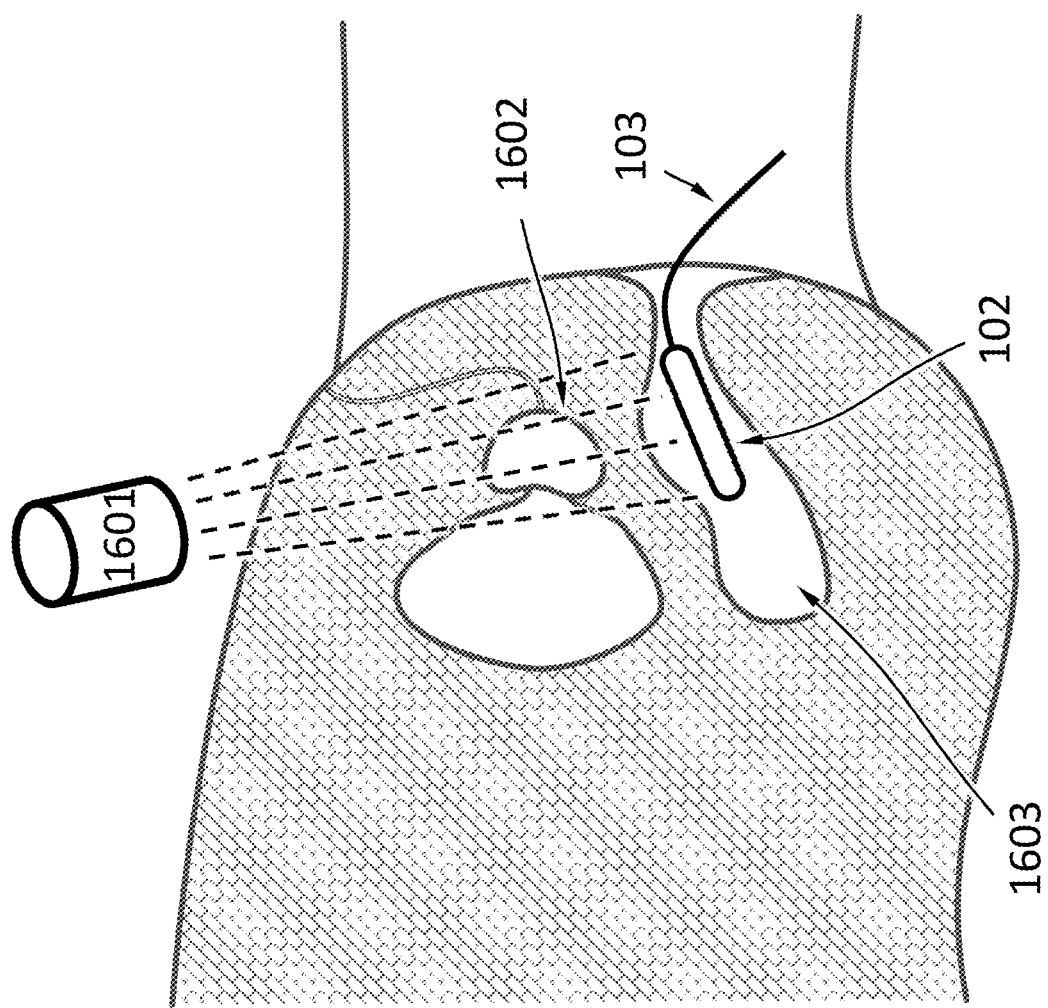
FIG. 8 schematically shows a system including the apparatus described above and a radiation source.

FIG. 8 schematically shows a system including the apparatus 101 described above and a radiation source 1601. The insertion tube 102 may be inserted into the rectum 1603 of a human. The radiation source 1601 may be configured to direct radiation toward the prostate 1602 in the human. The image sensor 100 forms an image of the prostate 1602 with the radiation. The system may be used for radiography on the prostate 1602.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. An apparatus comprising:
an insertion tube;
an image sensor inside the insertion tube;
wherein the image sensor comprises an array of pixels;
wherein the image sensor is configured to count numbers of particles of radiation incident on the pixels, within a period of time;
wherein the image sensor comprises:
a radiation absorption layer comprising an electric contact;
a first voltage comparator configured to compare a voltage of the electric contact to a first threshold;
a second voltage comparator configured to compare the voltage to a second threshold;
a counter configured to register at least one of the numbers;
a controller;
wherein the controller is configured to start a time delay from a time at which the first voltage comparator determines that an absolute value of the voltage equals or exceeds an absolute value of the first threshold;
wherein the controller is configured to activate the second voltage comparator during the time delay;
wherein the controller is configured to cause the at least one of the numbers to increase by one, when the second voltage comparator determines that an absolute value of the voltage equals or exceeds an absolute value of the second threshold;
wherein the radiation absorption layer comprises single-crystalline silicon.

2. The apparatus of claim 1, wherein the insertion tube is configured to be inserted into the rectum of a human.

3. The apparatus of claim 1, wherein the image sensor comprises a plurality of chips mounted on a substrate, wherein the pixels are distributed among the plurality of chips.

4. The apparatus of claim 1, wherein the image sensor is flexible.

5. The apparatus of claim 1, wherein the particles of radiation are X-ray photons.

6. The apparatus of claim 5, wherein the X-ray photons have energies between 20 keV and 30 keV.

7. The apparatus of claim 1, further comprising an integrator electrically connected to the electric contact, wherein the integrator is configured to collect charge carriers from the electric contact.

8. The apparatus of claim 1, wherein the controller is configured to activate the second voltage comparator at a beginning or expiration of the time delay.

9. The apparatus of claim 1, wherein the controller is configured to connect the electric contact to an electrical ground.

10. The apparatus of claim 1, wherein a rate of change of the voltage is substantially zero at expiration of the time delay.

11. The apparatus of claim 1, wherein the radiation absorption layer comprises a diode.

12. The apparatus of claim 1, wherein the image sensor does not comprise a scintillator.

13. A system comprising the apparatus of claim 1, and a radiation source.

14. A method comprising:
inserting, into the rectum of a human, an insertion tube with an image sensor therein, the image sensor comprising an array of pixels;
directing radiation toward the prostate of the human;
counting numbers of particles of radiation incident on the pixels, within a period of time;
obtaining an image of the prostate based on the numbers;
wherein the image sensor comprises:
a radiation absorption layer comprising an electric contact;
a first voltage comparator configured to compare a voltage of the electric contact to a first threshold;
a second voltage comparator configured to compare the voltage to a second threshold;
a counter configured to register at least one of the numbers;
a controller;
wherein the controller is configured to start a time delay from a time at which the first voltage comparator determines that an absolute value of the voltage equals or exceeds an absolute value of the first threshold;
wherein the controller is configured to activate the second voltage comparator during the time delay;
wherein the controller is configured to cause the at least one of the numbers to increase by one, when the second voltage comparator determines that an absolute value of the voltage equals or exceeds an absolute value of the second threshold;
wherein the radiation absorption layer comprises single-crystalline silicon.

15. The method of claim 14, wherein the image sensor comprises a plurality of chips mounted on a substrate, wherein the pixels are distributed among the plurality of chips.

16. The method of claim 14, wherein the image sensor is flexible.

17. The method of claim 14, wherein the particles of radiation are X-ray photons.

18. The method of claim 17, wherein the X-ray photons have energies between 20 keV and 30 keV.

19. The method of claim 14, wherein the image sensor further comprises an integrator electrically connected to the electric contact, wherein the integrator is configured to collect charge carriers from the electric contact.

20. The method of claim 14, wherein the controller is configured to activate the second voltage comparator at a beginning or expiration of the time delay.

21. The method of claim 14, wherein the controller is configured to connect the electric contact to an electrical ground.

22. The method of claim 14, wherein a rate of change of the voltage is substantially zero at expiration of the time delay.

23. The method of claim 14, wherein the radiation absorption layer comprises a diode.

24. The method of claim 14, wherein the image sensor does not comprise a scintillator.

* * * * *